United States Patent [19]

Patterson

[11] Patent Number: 4,622,305

[45] Date of Patent: Nov. 11, 1986

[54] METHOD OF THERMIONIC IONIZATION DETECTION OF CHEMICAL SUBSTANCES IN A GASEOUS ENVIRONMENT

[76] Inventor: Paul L. Patterson, 2212 Brampton Rd., Walnut Creek, Calif. 94598

[21] Appl. No.: 732,649

[22] Filed: Jun. 10, 1985

Related U.S. Application Data

[62] Division of Ser. No. 471,282, Mar. 2, 1983, Pat. No. 4,524,047.

[51] Int. Cl.$^4$ ............................................. G01N 27/62
[52] U.S. Cl. .................................... 436/103; 436/106; 436/153
[58] Field of Search ..................... 73/23; 324/468, 469; 338/34; 422/54, 70, 98; 436/149, 151, 153, 154, 161, 105, 103, 106

[56] References Cited

U.S. PATENT DOCUMENTS 4,203,726  5/1985  Patterson .......................... 422/98 X

OTHER PUBLICATIONS

Patterson et al; An Improved Thermionic Ionization Detector for Gas Chromatography, J. of Chrom. Sci., vol. 20, Mar. 1982.

*Primary Examiner*—David L. Lacey
*Assistant Examiner*—Michael S. Gzybowski
*Attorney, Agent, or Firm*—Leonard Bloom

[57] ABSTRACT

A method for analyzing specific chemical substances in a gaseous environment which utilizes a thermionic source formed of multiple layers of ceramic material composition, an electrical current instrumentality for heating the thermionic source to operating temperatures in the range of 100° C. to 1000° C., an instrumentality for exposing the surface of the thermionic source to contact with the specific chemical substances for the purpose of forming gas phase ionization of the substances by a process of electrical charge emission from the surface, a collector electrode disposed adjacent to the thermionic source, an instrumentality for biasing the thermionic source at an electrical potential which causes the gas phase ions to move toward the collector, and an instrumentality for measuring the ion current arriving at the collector. The thermionic source is constructed of a metallic heater element molded inside a sub-layer of hardened ceramic cement material impregnated with a metallic compound additive which is non-corrosive to the heater element during operation. The sub-layer is further covered by a surface-layer formed of hardened ceramic cement material impregnated with an alkali metal compound in a manner that eliminates corrosive contact of the alkali compounds with the heater element. The sub-layer further protects the heater element. The sub-layer further protects the heater element from contact with gas environments which may be corrosive. The specific ionization of different chemical substances is varied over a wide range by changing the composition and temperature of the thermionic source, and by changing the composition of the gas environment.

8 Claims, 2 Drawing Figures

METHOD OF THERMIONIC IONIZATION DETECTION OF CHEMICAL SUBSTANCES IN A GASEOUS ENVIRONMENT

This application is a division of application Ser. No. 471,282, filed Mar. 2, 1983, which has matured as U.S. Pat. No. 4,524,047 granted June 18, 1985.

BACKGROUND OF INVENTION

1. Field of Invention

This is a further development in the art of thermionic ionization detectors, and provides a method and apparatus for detecting specific chemical substances in a gaseous environment by ionizing these substances on the surface of a heated, multiple-layered thermionic source.

2. Prior art

Thermionic ionization detectors are used in the field of gas chromatography and elsewhere for the detection of specific chemical substances in a flowing gas stream. Such detectors usually consist of the following components: a thermionic source comprised of a surface impregnated with an alkali metal compound and heated electrically by means of a fine metallic heating wire embedded in the source; an electronic power supply capable of supplying an electrical heating current to the source; a collector electrode structure adjacent to but separated from the source; a gas stream flowing past the thermionic source; a means of electrically polarizing the source to cause either positive or negative ions formed on the surface of the source to migrate through the gas stream to the collector electrode; and an electronic current-measuring circuit such as an electrometer to measure the current arriving at the collector electrode. The single most important component in this detector is the thermionic source, and much of the prior art in thermionic detection techniques has dealt with methods of improving the construction and performance of the thermionic sources.

In 1951, Rice (U.S. Pat. No. 2,550,498) described a method and apparatus for electrically detecting vapors of certain substances by sensitizing a hot surface with a material from the class of alkali metals and their compounds. In Rice's apparatus, the heated sensitized surface consisted of a metallic heater coil wound on an alumina ceramic cylinder. Natural alkali impurities within the alumina ceramic served to produce the required sensitizing action for short operating times. Rice taught that the active life of the sensitized alumina could be increased or restored by soaking the alumina in a water solution containing an alkali metal salt. For even longer life, Rice further taught that the alumina cylinder could be replaced by a cylinder of alkali glass composition such as that described by Blewett (Physical Review, Vol. 50, p. 464, 1936).

In 1957, Roberts (U.S. Pat. No. 2,795,716) described an improved detector featuring a sensitized source having longer life compared to that described by Rice. Roberts' source consisted of a cylindrical alumina ceramic core upon which was wound a heater coil. The alumina core and heater coil were coated on their outer surfaces by a layer of "positive ion emitting material". This coating material was formed from an alkali glass which was powdered and mixed with a suitable ceramic cement in a desired proportion, then coated over the heating coil and alumina core and allowed to set.

In 1975, Kolb and Bischoff (U.S. Pat. No. 3,852,037) described a selective ionization detector which used an alkali glass material deposited in the form of a bead onto an electrical heating wire. Kolb and Bischoff argued that successful detection required operating the alkali glass in a heated, softened state such that molecular motion within the body of the bead acted to maintain an adequate supply of alkali material at the bead surface. Kolb and Bischoff collected negative ionization whereas the earlier devices of Rice and Roberts collected positive ionization.

In 1977, Burgett et. al. (Journal of Chromatography, Vol. 134, p. 57, 1977), described a nitrogen-phosphorus specific detector which used an electrically heated source comprised of a ceramic cylinder core coated with a surface layer of an alkali salt activator similar to the alkali-glass described earlier by Rice. In Burgett's source, a segment of the heating coil was embedded in the ceramic core, and positive ions were collected.

In 1978, Patterson (Journal of Chromatography, Vol. 167, p. 381, 1978) presented data demonstrating that the ionization mechanism in these thermionic detectors was a surface ionization process rather than a gas phase process. According to Patterson, sample compounds or their decomposition products extract electrical charge from the hot thermionic surface, and the resulting ionization is collected at an adjacent electrode. For such a surface ionization process, the three most important operating parameters in the detector were identified to be the work function of the thermionic surface, the temperature of the surface, and the chemical composition of the gas environment surrounding the surface.

In 1980, Patterson (U.S. Pat. No. 4,203,726) described a thermionic detector in which the source was formed from a homogeneous mixture of an alkali metal compound and a ceramic cement coated directly over a helical shaped heating coil. In this case, the alkali-ceramic material formed the entire body of the source rather than just the surface layer. Similar to Kolb and Bischoff, it was argued that the presence of alkali material within the body of the source helped promote longer source operating life by providing a reservoir for replenishing the alkali concentration at the source's surface.

In 1982, Patterson (Journal of Chromatographic Science, Vol. 20, p. 97, 1982) described a thermionic source which contained a separate metallic heating wire and a separate metallic temperature sensing wire. The two separate wires were contained in a four-hole alumina ceramic cylindrical core, and the surface of the core was coated with an activating alkali-ceramic mixture. The advantage of this source construction was that it provided a means of controlling the source temperature with a constant temperature electronic circuit rather than a constant circuit.

Since the mechanism of ionization in the thermionic detector is a surface ionization process, most of the prior art has concentrated on the development of suitable surface compositions in order to obtain the specific responses of the detector. However, in addition to the surface ionization, there must also occur a process of charge migration in the source in order to replace the electrical charge lost from the surface. This charge migration can be described as a current originating at the metallic heating wire and flowing through the body of the source to its surface. For the prior art devices in which the source was composed of a homogeneous composition of an alkali-glass or alkali-ceramic formulation, the presence of alkali material in the source body facilitated the flow of current through the source body.

However, such alkali-glass or alkali-ceramic compositions were chosen primarily for their surface ionization characteristics and did not necessarily provide the most optimum medium for the process of charge migration through the source body. A particular disadvantage of these homogeneous source compositions was that the hot metallic heating element was exposed to corrosive attack by direct contact with alkali atoms.

This corrosion problem was minimized by those prior art devices in which the heating element was embedded in an inert alumina ceramic core and the alkali-glass or alkali-ceramic sensitizing material was present in the form of a surface layer on the core. However, in these devices, the core material was not conducive to the conduction of current through the source body. Consequently, a newly constructed source with an inert alumina ceramic core, generally had to be conditioned at operating temperatures for a time of approximately 24 hours or more before the desired detector responses were obtained. During this conditioning period, it could be postulated that there occurred some permeation of alkali material from the source surface layer into the source core, thereby enhancing the electrical conductivity of the core until some equilibrium condition was reached. Therefore, charge migration through the body of the resultant conditioned source was dependent on the composition of the alkali-impregnated surface layer as well as on the operating conditions used during the conditioning period.

In the 1982 prior art device described by Patterson, the metallic heating wire was contained inside two of four tubular holes in an alumina ceramic cylindrical core. Since these tubular holes had to be of larger internal diameter than the diameter of the heating wire in order to allow the heating wire to be guided through the alumina core, a continuous physical contact of the heating wire and the alumina core could not be ensured. This undefined extent of physical contact presented a further negative variance affecting the migration of charge from the heating wire, through the alumina core to the alkali-impregnated surface layer.

In some of the prior art devices, the thermionic sources were constructed in such a manner that portions of the metallic heating wires were not coated with the alkali-glass or alkali-ceramic material, nor with any insulating material. Since the metallic heating wires were typically wires of very small diameter, such exposed fine wires were often subject to mechanical breakage during installation or operation of the source. Also, such exposed wires were subject to corrosion from various chemicals present in the gas stream being measured.

SUMMARY OF THE INVENTION

This invention provides a method and apparatus for the thermionic ionization detection of specific chemical substances in a gaseous environment. In the thermionic ionization technique, substances to be measured are directed in a gas stream such that they impinge upon the surface of a heated and appropriately sensitized thermionic source. The substances in question are ionized by means of a surface ionization process in which electrical charge is removed from the thermionic source and is converted into gas phase ion species. Under the influence of an applied electrical field, the current of gaseous ions is collected and measured at a collector electrode adjacent to the thermionic source. The type of signal response obtained in this detection method is dependent on the following parameters:

1. the composition and the work function of the surface of the thermionic source;
2. the surface temperature of the thermionic source;
3. the chemical composition of the gaseous environment surrounding the thermionic source;
4. and the electronegative nature of the substances being measured or the electronegative nature of their decomposition products in the case where the substances are decomposed in a hot, chemically reactive gaseous boundary layer surrounding the thermionic source.

Through variations in the chemical composition of the thermionic source, the surface temperature of the source, and the chemical composition of the gas environment, the detector response to various types of substances can be significantly changed over a very wide range. Since there are possible many permutations of source composition, source temperature, and gas environment composition, there are also possible many different modes of thermionic ionization detection.

It is a particular object of this inventon to provide a method of separately adjusting the composition of the thermionic source for the control of the two distinct processes of charge migration through the source body, and surface ionization at the source surface. Separate control of these two different physical processes is accomplished by forming the thermionic sources in separate layers of different chemical composition. Each layer is formed by mixing together a ceramic cement material and one or more inorganic chemical additives. To promote charge migration through the body of the thermionic source, the sources are comprised of one or more sub-layers containing chemical additives that increase the electrical conductivity of the additive-ceramic cement mixture above that of the ceramic cement material alone. This sub-layer is then covered with a surface layer containing ceramic cement material and alkali-metal additives chosen to produce a specific type of surface ionization. With both the sub- and surface-layers of the thermionic sources being composed of ceramic-type material, the resultant sources are capable of operating at temperatures up to 1000° C. without melting. Also, the method of forming sources from mixtures of ceramic cement material and various additives allows a very wide variety of additives to be used for both the sub-layer and surface layer. The basic requirements for the chemical additives are that they must be capable of being reduced to a powder form, and they must not have vaporization temperatures lower than the intended operating temperature of the source. This layered method of forming the source makes possible the variation of surface ionization characteristics through changes in composition of the surface layer, while at the same time the charge migration through the source body may be held constant by maintaining a fixed composition for the sub-layer. Similarly, the surface layer composition can be held fixed, and the sub-layer composition varied to change the charge migration through the source body. Therefore, this layered method of forming the themionic sources provides a means of controlling all the charge transport processes active in the source to a greater degree than previously has been possible. One positive outcome of this method of forming sources is that newly constructed source typically exhibits a conditioning time of one hour or less until the desired detector responses are obtained.

It is also a particular object of this invention to provide a method of minimizing corrosive attack of the metallic heating wire in thermionic sources by completely covering that wire with a layer of non-corrosive material. Many applications of thermionic ionization detectors require thermionic sources which have significant concentrations of alkali-metal compounds in their surface composition. These alkali compounds are corrosive to the hot metallic heating wire if there is direct contact between the wire and the alkali compounds. This contact is avoided by forming the thermionic sources in a layered manner in which the metallic heating wire is completely covered with a sub-layer comprised of non-corrosive ceramic material or a mixture of ceramic material and an inorganic, electrically conductive and non-corrosive chemical additive. The alkali-metal compounds or other corrosive compounds required for a particular surface ionization process are then contained only in a surface layer coating on the thermionic source, and these corrosive compounds do not have direct contact with the metallic heating wire. One particular advantage of covering the metallic heating wire with a non-corrosive sub-layer, is that a greater variety of chemical additives can be used in the surface layer of the source without concern whether these additives will rapidly corrode the metallic heating wire. This advantage provides a new degree of freedom in varying surface-layer compositions so as to extend the modes of thermionic ionization detection beyond those previously attainable. Another positive consequence of the non-corrosive sub-layer is that the source can be recoated with a new surface layer when the surface activity has been diminished by use. This recoating has not been practical in many prior art devices because of the occurrence of corrosion of the metallic heating wire with usage.

It is also a particular object of this invention to provide a thermionic source structure which does not leave exposed any portion of the small diameter metallic heating wire, so as to minimize mechanical breakage of the wire upon installation and operation of the thermionic source, and to minimize corrosion from various chemicals present in the gas stream being measured. This allows a wider variety of gas stream compositions to be used than has been possible in previous devices. A particular advantage is that gas stream compositions which are highly chemically reactive can be used as a further means of varying the specific ionization processes occurring on the surface of the thermionic source.

DESCRIPTION OF PREFERRED EMBODIMENTS

Figure 1:
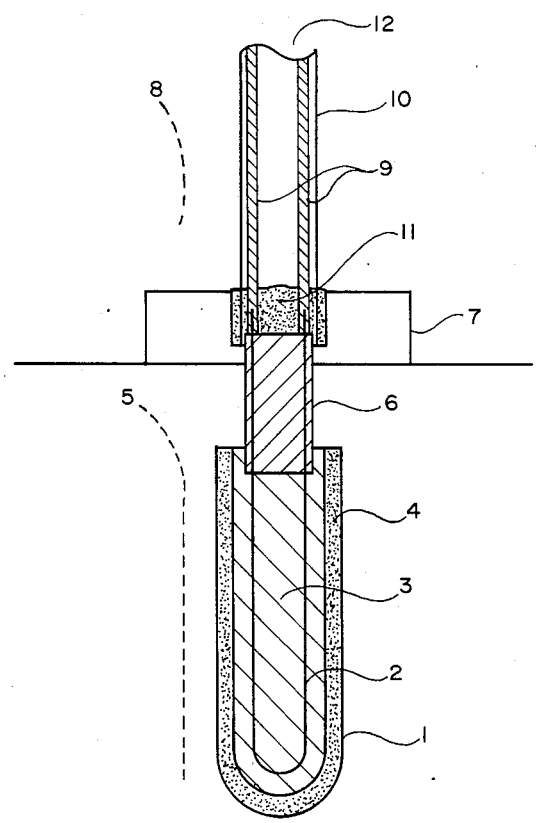
FIG. 1 is a schematic illustration of the construction of thermionic sources according to the present invention.

FIG. 1 shows a schematic, cross sectional view of a thermionic source constructed according to the present invention. A ceramic, thermionic source structure 1 of cylindrical shape is molded about a loop or coil of a metallic heating element 2 formed of nichrome or platinum wire. The thermionic source structure 1 is comprised of a sub-layer 3 formed from a coating mixture of ceramic cement and a non-corrosive, metallic compound additive, and a surface layer 4 formed from a mixture of ceramic cement and an alkali metal compound additive. The presence of alkali metal atoms in the surface layer produces a surface of low work function which is capable of emitting electrical charge at elevated temperatures of the thermionic source 1. In a typical operation, the source 1 is heated to temperatures in the range of 100° C. to 1000° C. by passing an electrical current through the heater element 2. The purpose of the sub-layer 3, is to protect the metallic heater element from chemically corrosive attack by alkali atoms from the surface layer 4, and to provide a source body through which electrical charge can migrate from the heater element to the surface layer in order to replace charge lost from the surface by the emission process. In operation, the thermionic source 1 is exposed to a gas environment 5 containing sample compounds which are electronegative in chemical structure. Such sample compounds readily form gas phase negative ions by the attachment of electrons or negative ions. When such compounds impinge on the surface layer 4 of the thermionic source 1, they are ionized by extracting negative charge from the surface of the source.

Since the gas environment 5 and sample compounds which are exposed to the thermionic source 1 are also potentially corrosive to the metallic heater element 2, the element 2 is further protected by enclosure within a sealed ceramic tubing 6 until the element 2 passes into the interior of a flange structure 7. In some applications, the flange 7 may be attached to a gas containment vessel such that it separates the sampled gas environment 5 from an ambient gas environment 8. Within the flange 7, the two ends of the small diameter heater wire 2 are attached to two electrical lead wires 9 of lower electrical resistance, and these lead wires are insulated from the ambient gas environment by a fiberglass sleeve of insulation 10. The junction of heater elements 2 and lead wires 9, as well as the end of the fiberglass sleeve 10 are all affixed to the flange structure 7 by sealing in a ceramic cement 11. The insulated electrical lead wires are then extended 12 through an ambient gas environment 8 to an ambient temperature connection with an electronic power supply. The thermionic source shown in FIG. 1 illustrates a construction method which completely encloses the heater element 2 from potentially corrosive contact with either the alkali compounds in the surface layer 4 or the corrosive gas environment 5. It also provides a thermionic source structure which is mechanically rigid and strong.

In a preferred embodiment of the present invention, a nichrome wire having a diameter of 0.010 inches is used as the heater element 2. This wire is formed into a loop shape and the two ends of the wire are guided through a cylindricallyshaped ceramic insulator tube 6 comprised of alumina ceramic material and containing two tubular holes of diameters 0.016 inches each. The outside diameter of the ceramic insulator 6 is 0.062 inches and its approximate length is 0.45 inches. An exposed loop of the heater element 2 extends a length of approximately 0.20 inches beyond the end of the ceramic insulator 6. This exposed loop is covered with a sub-layer 3 and surface layer 4 coating having a maximum outer diameter less than 0.080 inches. These dimensions are not to be considered restrictive, and larger or smaller dimensions can be used with corresponding adjustments in the magnitude of electrical current supplied to heat the thermionic source.

The sub-layer ceramic coating 3 which is molded about the exposed loop of the heater element 2 is formed from a slurry consisting of a mixture of proportionate amounts of water, ceramic cement, and a metallic compound additive. This slurry is applied in a manner such that it overlaps a portion of the ceramic insulator 6 and the coating is of sufficient thickness that all lengths of the exposed loop of heater element 2 are completely covered by the slurry coating. When appropriately cured, the resultant sub-layer coating provides a mechanically rigid and solid protective coating for the heater element.

The ceramic cement used in this application preferably contains 100% inorganic constituents such as $Al_2O_3$ or $AlSiO_2$. Preferred characteristics of the ceramic cement are that it withstand temperatures in excess of 1000° C.; that it be non-porous and make gas tight seals; that it form highstrength bonds; that it resist thermal shock; and that it exhibit low shrinkage. Cements of this type are commercially available in dry powder form. An example of a suitable ceramic cement is Ceramacast Type 505 Cement manufactured by AREMCO Products, Inc. of Ossining, N.Y.

A main function of the sub-layer coating 3 is to prevent corrosive contact of the heater element 2 with alkali metals or other corrosive species present in the surface layer 4 of the thermionic source 1. Therefore, any inorganic chemical compounds added to the ceramic cement in forming the sub-layer coating 3 must be non-corrosive to the heater element 2 when that element is operated at temperatures as high as 1000° C. Specifically, alkali metal compounds or halogenated compounds are excluded because of their corrosive properties.

A second function of the sub-layer coating 3 is to provide a solid medium through which electrical charge can migrate from the heater element 2 to the surface layer 4 of the thermionic source in order to replace charge lost from the surface by thermionic emission processes. For this purpose, inorganic chemical compounds added to the ceramic cement in forming the sub-layer coating 3 are metallic compounds which increase the electrical conductivity of the additive-ceramic cement mixture above the electrical conductivity of the ceramic cement alone. One required physical property of the metallic compound additive is that it be available in powder form in order to allow a finely divided homogeneous mixture with the powder form of the ceramic cement. For the purpose of this invention, the sub-layer coating mixture contains metallic compound additives at proportionate amounts exceeding 2% by weight of the ceramic cement used. The maximum proportionate amount of metallic additive that can be included in the sub-layer mixture is determined by the proportionate ratio at which the cured coating mixture ceases to be a mechanically hard substance. Experimentation has shown that this maximum limit for the metallic additive is approximately 25% by weight of the ceramic cement used. One sub-layer composition that has proven successful is a mixture of 18% by weight of nickel powder and 82% by weight ceramic cement. This proportionate amount and the specification of a nickel additive are not to be considered as restrictive conditions for forming suitable sub-layers. In the periodic table of chemical elements, there are many other metallic species having the required characteristics of being non-corrosive to the heater element and being available in powder form either as the pure metal or as an inorganic metallic compound.

The surface layer 4 is formed from a slurry consisting of a mixture of proportionate amounts of water, ceramic cement, and an alkali-metal compound. This slurry is coated over the previously cured and hardened sub-layer coating 3. This surface coating is then appropriately cured to form a hardened surface for the thermionic source. The amount and type of alkali metal compound used in the surface layer 4 are selected according to the intended type of surface ionization process sought. For example, one surface composition consisting of 4% by weight of $Cs_2SO_4$ and 92% by weight of ceramic cement is used in a hot, chemically reactive gas environment of dissociated $H_2$ and $O_2$ to provide specific ionization of sample compounds containing nitrogen or phosphorus atoms. Another surface composition consisting of 20% by weight of $Cs_2SO_4$ and 80% by weight of ceramic cement is used in an inert gas environment of $N_2$ to provide specific ionization of sample compounds which are electronegative, and especially compounds containing the $NO_2$ group or the SH group, and some polychlorinated compounds. The surface composition consisting of 20% by weight of $Cs_2SO_4$ and 80% by weight of ceramic cement also provides specific responses to most halogenated compounds when operated in a gas environment of air or $O_2$. In general, alkali metal compound additives in proportionate amounts ranging from 1% by weight to 25% by weight in the surface layer composition exhibit useful ionization characteristics under various operating conditions of the thermionic source 1. These additives may include compounds of any of the class of alkali metals which includes Cs, Rb, K, Na, and Li, and in some instances may include a combination of more than one type of alkali metal compound. Specific requirements for the alkali metal compounds used are that they must be capable of being reduced to a powder form and they must have a low volatility at the intended operating temperature of the thermionic source. Alkali sulfate compounds have been found to be especially suitable. Other kinds of alkali compounds that might be used include alkali carbonates and alkali chlorides. The method of the present invention which protects the heater element 2 from contact with the surface layer 4 allows alkali compounds, halogenated compounds, and other potentially corrosive compounds to be used as surface layer constituents without destroying the heater element.

Figure 2:
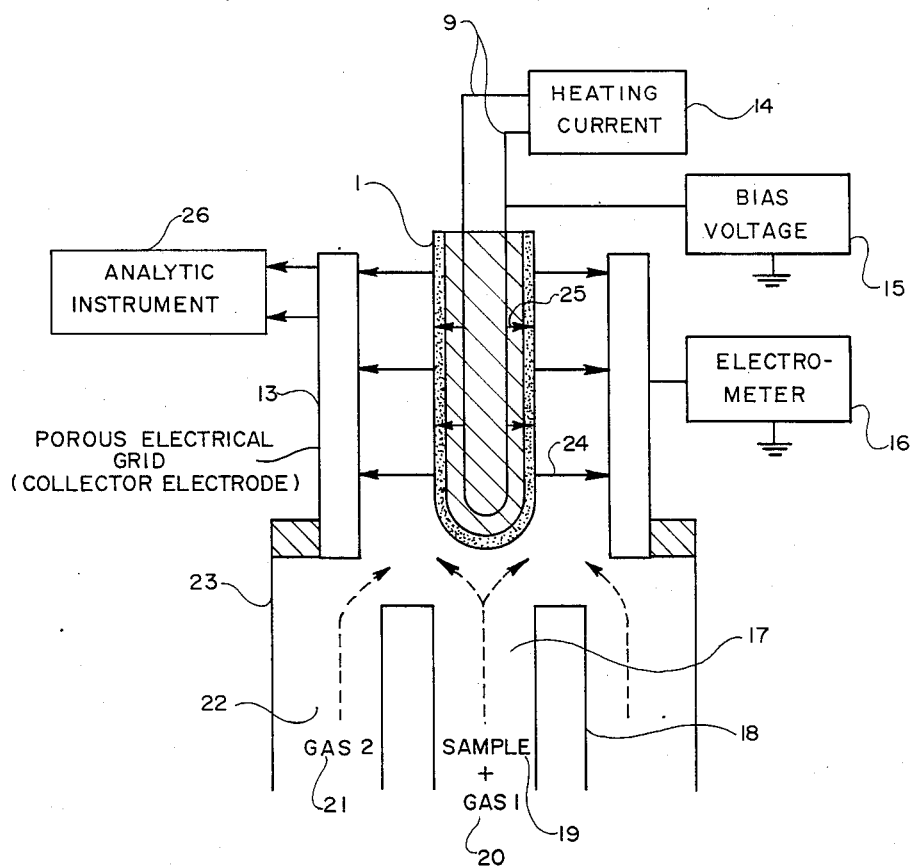
FIG. 2 is a schematic illustration of the electronic connections to the thermionic source when it is used as a detector of specific chemical species.

FIG. 2 shows a schematic illustration of the electronic and mechanical components of a detector which uses the thermionic source of the present invention. The cylindrically shaped thermionic source 1 is positioned coaxially in the center of a metal collector electrode 13 of cylindrical shape.

The collector electrode 13 is preferably a porous metal grid. The two electrical leads 9 from the thermionic source are connected to an electronic power supply that provides a source of electrical current 14 for the purpose of heating the heater element 2. The electronic power supply also provides a bias voltage 15 which fixes the electrical potential of the thermionic source 1 at a negative magnitude relative to the surrounding collector electrode 13. The collector electrode 13 is electrically connected to an electrometer 16 which is used to measure the magnitude of ionization current that arrives at the collector.

The most versatile configuration of a thermionic ionization detector which uses the thermionic source of the present invention, exposes that source 1 to a gas environment that is generated by controllable gas flows originating from three different gas supplies. A center passageway 17 through an inner cylindrical structure 18 provides a conduit for directing a mixture of a sample gas flow 19 and one additional detector gas flow 20 to the proximity of the thermionic source 1. A separate detector gas flow 21 is also directed to the proximity of the thermionic source via an outer annular passageway 22 between the inner cylindrical structure 18 and an outer cylindrical structure 23. In one common application of this type of thermionic ionization detector, the sample gas flow 19 is the effluent gas stream of a gas chromatograph instrument. In some applications, the two detector gas flows 20 and 21 are gases of different composition, while in other applications gases 20 and 21 are the same composition. The construction of the thermionic source in the present invention also allows the use of gas compositions which would be corrosive to the heater element 2 if it were exposed to direct contact with the gas environment.

In operation, sample compounds in the sample gas flow 19 impinge upon the heated surface of the thermionic source 1. Certain types of sample compounds form gas phase negative ions by extraction of negative electrical charge from the thermionic surface, and these negative ions cause an electrical current flow 24 to the collector 13. This negative ionization current is measured with the electrometer 16. To replace the electrical charge emitted from the surface of the thermionic surface, there must also occur a corresponding migration of charge 25 which originates at the heater element 2 and passes through the solid body of the thermionic source to the surface layer.

The surface ionization process which is the basic mechanism of operation of this type of thermionic ionization detector is determined by three main parameters, as follows:

1. the chemical composition of the thermionic surface;
2. the temperature of the thermionic surface;
3. and the chemical composition of the gas environment surrounding the surface.

Variations in any or all of these three parameters can result in significant changes in the types of sample compounds detected by this thermionic means. The thermionic source of the present invention is formed of ceramic materials that can withstand variations in temperatures over a wide range. Also, the complete covering of the heater element 2 by non-corrosive materials allows a wide range of surface compositions and gas environments to be used without corrosion of the heater element.

The thermionic sources of the present invention are not limited in application to use as thermionic ionization detectors in gas chromatograph instruments. Since these thermionic sources provide selective ionization of only certain types of chemical substances, these sources can also be used in the detection of the presence of these specific chemical substances in any gas environment. It is also recognized that the thermionic sources of the present invention can be used as a means of converting molecules of certain types of chemical substances into gas phase negative ions for the purpose of subsequent analysis of charge-to-mass ratio by a mass spectrometer instrument, or mass and size analysis by an ion mobility apparatus. For such applications, the collector electrode 13 would have the form of a porous electrical grid to allow the passage of gas phase ions into the subsequent analysis equipment. The possibility of effecting further ion analysis is illustrated diagramatically in FIG. 2 by an analytic instrument 26 positioned to received ions from the porous electrical grid.

The preferred embodiment of this invention has been described in terms of the measurement of electrical current of negative polarity. However, there are some applications where the collection of positive rather than negative ionization may be appropriate, as has been demonstrated in some prior art devices of this type. The advantages of a multiple-layered construction of the thermionic source are applicable for either positive or negative ion collection.

This invention has been described in terms of a preferred embodiment. It is to be recognized, however, that variations in the composition of the thermionic sources and modifications in the dimensions or configuration of the thermionic detector might be appropriate for certain applications and yet be within the scope of this invention. Accordingly, this invention is to be broadly construed, and is limited only by the following claims.

I claim:

1. A method of thermionic ionization detection of chemical substances in a gaseous environment, said method comprising the steps of:

electrically heating a thermionic source having a surface in a gaseous environment to operating temperatures in the range of from about 100° C. to about 1,000° C., said thermionic source comprising a metallic heater element, a first coating layer covering said heater element, said first coating layer comprising a hardened ceramic cement material which includes a non-alkali metal therein which is non-corrosive to said heater element at said operating temperatures, a second coating layer covering said first coating layer, said second coating layer comprising a hardened ceramic cement material impregnated with an alkali metal compound, the materials used in said heater element and said first and second coating layers all being capable of withstanding operating temperatures up to about 1,000° C.;

causing chemical substances to interact with the surface of said thermionic source to form gas phase ions of said chemical substances by emission of electrical charge from said surface of said thermionic source;

maintaining a collector electrode in said gaseous environment adjacent said thermionic source;

maintaining a difference of electrical potential between said heater element and said collector electrode to cause said gas phase ions to move toward said collector electrode , and to cause a migration of electrical charge from said heater element through said first and second coating layers to replace the charge emitted from the surface of said thermionic source; and measuring said gas phase ionization current to detect the presence of said chemical substances.

2. The method of claim 1 wherein said gaseous environment adjacent to said thermionic source is chemically inert.

3. The method of claim 1 wherein said chemical substances have chemical structures which are electronegative.

4. The method of claim 1 wherein said chemical substances contain a nitrogen atom.

5. The method of claim 1 wherein said chemical substances contain a phosphorus atom.

6. The method of claim 1 wherein said gaseous environment adjacent to said thermionic source is chemically reactive.

7. The method of claim 6 wherein said chemical reactivity of said gaseous environment is caused by the high temperature of said thermionic source.

8. The method of claim 7 wherein said chemical reactivity of said gaseous environment is further caused by dissociation of molecular hydrogen and oxygen gases at high temperatures.

* * * * *